(12) United States Patent
Shapero

(10) Patent No.: US 8,728,767 B2
(45) Date of Patent: *May 20, 2014

(54) METHOD OF OLIGONUCLEOTIDE SYNTHESIS

(75) Inventor: Michael Shapero, Redwood City, CA (US)

(73) Assignee: Affymetrix, Inc., Santa Clara, CA (US)

( * ) Notice: Subject to any disclaimer, the term of this patent is extended or adjusted under 35 U.S.C. 154(b) by 1338 days.

This patent is subject to a terminal disclaimer.

(21) Appl. No.: 11/962,715

(22) Filed: Dec. 21, 2007

(65) Prior Publication Data

US 2010/0311128 A1    Dec. 9, 2010

Related U.S. Application Data

(63) Continuation of application No. 10/741,068, filed on Dec. 19, 2003, now Pat. No. 7,314,714.

(51) Int. Cl.
*C12Q 1/68* (2006.01)
*C07H 21/04* (2006.01)

(52) U.S. Cl.
USPC ........ 435/91.5; 435/91.2; 536/23.1; 536/25.3

(58) Field of Classification Search
None
See application file for complete search history.

(56) References Cited

U.S. PATENT DOCUMENTS

| | | | |
|---|---|---|---|
| 5,242,794 A | 9/1993 | Whiteley et al. | |
| 5,256,549 A * | 10/1993 | Urdea et al. | 435/91.1 |
| 5,455,166 A | 10/1995 | Walker | |
| 5,470,723 A | 11/1995 | Walker et al. | |
| 5,523,204 A | 6/1996 | Singer et al. | |
| 5,561,044 A | 10/1996 | Walker et al. | |
| 5,631,147 A | 5/1997 | Lohman et al. | |
| 5,648,211 A | 7/1997 | Fraiser et al. | |
| 5,712,124 A | 1/1998 | Walker | |
| 5,736,365 A | 4/1998 | Walker et al. | |
| 5,744,311 A | 4/1998 | Fraiser et al. | |
| 5,856,092 A | 1/1999 | Dale et al. | |
| 5,874,260 A | 2/1999 | Cleuziat et al. | |
| 5,916,779 A | 6/1999 | Pearson et al. | |
| 5,935,793 A | 8/1999 | Wong | |
| 5,952,174 A | 9/1999 | Nikiforov et al. | |
| 6,017,738 A | 1/2000 | Morris et al. | |
| 6,087,133 A | 7/2000 | Dattagupta et al. | |
| 6,191,267 B1 | 2/2001 | Kong et al. | |

(Continued)

FOREIGN PATENT DOCUMENTS

EP        500224 A2    8/1992
EP        676476 A1   10/1995

(Continued)

OTHER PUBLICATIONS

Shibahara et al. Inhibition of human immunodeficiency virus (HIV-1) replication by synthetic olig-RNA derivatives. Nucleic Acids Research 17(1):239-252 (1989).*

(Continued)

*Primary Examiner* — Samuel Woolwine
(74) *Attorney, Agent, or Firm* — Banner & Witcoff, Ltd.

(57) ABSTRACT

Methods and kits for synthesizing a plurality of oligonucleotides are provided. Methods for providing a plurality of oligonucleotides enriched for full length oligonucleotides are provided. Truncated oligonucleotides are preferentially removed from the sample by digestion. Methods are also provided for amplification of a plurality of oligonucleotides.

23 Claims, 3 Drawing Sheets

(56) References Cited

U.S. PATENT DOCUMENTS

| | | | |
|---|---|---|---|
| 6,214,587 B1 | 4/2001 | Dattagupta et al. | |
| 6,238,868 B1 | 5/2001 | Carrino et al. | |
| 6,531,302 B1 | 3/2003 | Nerenberg et al. | |
| 6,638,719 B1 | 10/2003 | Gunderson et al. | |
| 6,709,816 B1 | 3/2004 | Huang et al. | |
| 6,864,071 B2 | 3/2005 | Carrino et al. | |
| 6,867,028 B2 | 3/2005 | Janulaitis et al. | |
| 6,867,294 B1 | 3/2005 | Sanghvi et al. | |
| 6,884,586 B2 | 4/2005 | Van Ness et al. | |
| 2003/0104430 A1 | 6/2003 | Nerenberg et al. | |
| 2003/0211506 A1 | 11/2003 | Kong et al. | |
| 2003/0232348 A1 | 12/2003 | Jones et al. | |
| 2004/0076994 A1* | 4/2004 | Yaku et al. | 435/6 |
| 2004/0115644 A1 | 6/2004 | Dong | |
| 2007/0059692 A1* | 3/2007 | Gao et al. | 435/6 |

FOREIGN PATENT DOCUMENTS

| | | |
|---|---|---|
| EP | 819768 A2 | 1/1998 |
| EP | 713922 B1 | 9/1999 |
| WO | WO 20053617 | 9/2000 |

OTHER PUBLICATIONS

Applied Biosystems, DNA/RNA Synthesizers Models 392 and 394 User's Manual. 16 pages total, Jun. 2001.

Caruters et al; "Chemical synthesis of deoxyoligonucleotides by the phosphoramidite method". Methods Enzymol. 1987; 154:287-313.

Claeboe et al. "3'-modified oligonucleotides by reverse DNA synthesis." Nucleic Acids Res. Oct. 1, 2003;31(19):5685-91. Nucleic Acids Res. Oct. 1, 2003;31(19):5685-91.

Debear et al; "A universal glass support for oligonucleotide synthesis"; Nucleosides & Nucleotides6(5); pp. 821-830 (1987).

Engler and Richardson. "Bacteriophage T7 DNA replication. Synthesis of lagging strands in a reconstituted system using purified proteins." J Biol Chem. Sep. 25, 1983;258(18):11197-205.

Nikiforov et al. "The use of phosphorothioate primers and exonuclease hydrolysis for the preparation of single-stranded PCR products and their detection by solid-phase hybridization." PCR Methods Appl. Apr. 1994;3(5):285-91.

Ravikumar et al. "Antisense phosphorothioate oligodeoxyribonucleotide targeted against ICAM-1: synthetic and biological characterization of a process-related impurity formed during oligonucleotide synthesis." Bioorg Med Chem. Oct. 15, 2003;11(21):4673-9.

Spargo et al; "Detection of M. Tuberculosis DNA using thermophilic strand displacement amplification"; Mol Cell Probes. Aug. 1996; 10(4):247-56.

Syvanen. "Accessing genetic variation: genotyping single nucleotide polymorphisms." Nat Rev Genet. Dec. 2001;2(12):930-42.

Zhu et al, "Engineering strand-specific DNA nicking enzymes from the type IIS restriction endonucleases BsaI, BsmBI, and BsmAI"; J. Mol Biol. Mar. 26, 2004; 337(3):573-83.

* cited by examiner

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (42)..(45)
<223> OTHER INFORMATION: n is a, c, g, or t

<400> SEQUENCE: 1
cttgtctggt cccacagttc tccctttagt gagggttaat tnnnngatcc              50

<210> SEQ ID NO 2
<211> LENGTH: 41
<212> TYPE: DNA
<213> ORGANISM: Artificial
<220> FEATURE:
<223> OTHER INFORMATION: Synthetic DNA
```

```
<400> SEQUENCE: 2
aattaaccct cactaaaggg agaactgtgg gaccagacaa g                    41
```

METHOD OF OLIGONUCLEOTIDE SYNTHESIS

This application is a continuation of U.S. patent application Ser. No. 10/741,068, filed Dec. 19, 2003 which is incorporated by reference for all purposes.

FIELD OF THE INVENTION

The methods of the invention relate generally to synthesis of a plurality of oligonucleotide sequences. The methods provide for enriching a plurality of synthesized oligonucleotides that comprises truncated and full length oligonucleotides for full length oligonucleotides. Methods for amplification of full length oligonucleotides in the enriched sample are also disclosed.

BACKGROUND OF THE INVENTION

Synthesis of large numbers of different oligonucleotide sequences on solid supports has been described previously, see for example, Fodor et al., *Science* 251(4995), 767-73, 1991, Fodor et al., *Nature* 364(6437), 555-6, 1993 and Pease et al. *PNAS USA* 91(11), 5022-6, 1994 and U.S. Pat. No. 5,445,934.

SUMMARY OF THE INVENTION

In one embodiment a method of making a plurality of oligonucleotides that is enriched for full length oligonucleotides is disclosed. A plurality of oligonucleotides is synthesized on a solid support so that the oligonucleotides are attached to the solid support by a cleavable linker, for example uracil, and the 5' end of the full length oligonucleotides includes an element that confers nuclease resistance, for example, phosphorothioate linkages. After cleaving the linker to release the oligonucleotides from the solid support, a primer is hybridized to the 3' end of the released oligonucleotides and extended to generate double stranded oligonucleotides. Truncated oligonucleotides are then digested, for example, by adding a 5' to 3' exonuclease such as T7 gene 6 exonuclease. The oligonucleotides that are at least a specified length, full length oligonucleotide, are resistant to digestion because they include the nuclease resistant element. After digestion the sample is enriched for full length oligonucleotides. In a preferred embodiment more than 1000 different sequence oligonucleotides are synthesized simultaneously.

In a preferred embodiment four phosphorothioate linkages are incorporated into the 5' end of the oligonucleotide, resulting in nuclease resistance.

In another embodiment a method of amplifying a plurality of sequences of interest is disclosed. A plurality of template oligonucleotides is synthesized on a solid support. The template oligonucleotides are attached to the solid support by a cleavable linker and the full length template oligonucleotides include a 5' element that confers nuclease resistance. The cleavable linker is cleaved to release the template oligonucleotides from the solid support. A primer is hybridized to the 3' end of the released template oligonucleotides and extended to make the template oligonucleotides double stranded. In a preferred embodiment oligonucleotides that are not full length are digested with an exonuclease. The double stranded template oligonucleotides are nicked near the 5' end of one strand, thereby generating a 5' and a 3' portion of one strand, wherein the 3' portion comprises a sequence of interest, and the 5' portion is extended with a strand displacing enzyme wherein the 3' portion is released and a new copy of the 3' portion is synthesized.

In a preferred embodiment the method may be used to amplify at least 1000 different sequences of interest. Each sequence of interest may include a common adaptor sequence and a locus specific sequence. Nicking may be by a nicking restriction enzyme, such as BstNB1. In another embodiment one strand of the double stranded oligonucleotide may be blocked from cleavage, for example by a phosphorothioate linkage, and the nicking may be by a restriction enzyme that cleaves double stranded nucleic acid. In a preferred embodiment cleavage and extension take place in the same reaction and are preferably repeated multiple times, releasing the 3' portion each time, thereby amplifying the 3' portion.

DETAILED DESCRIPTION OF THE PREFERRED EMBODIMENTS

A) General

Figure 1:
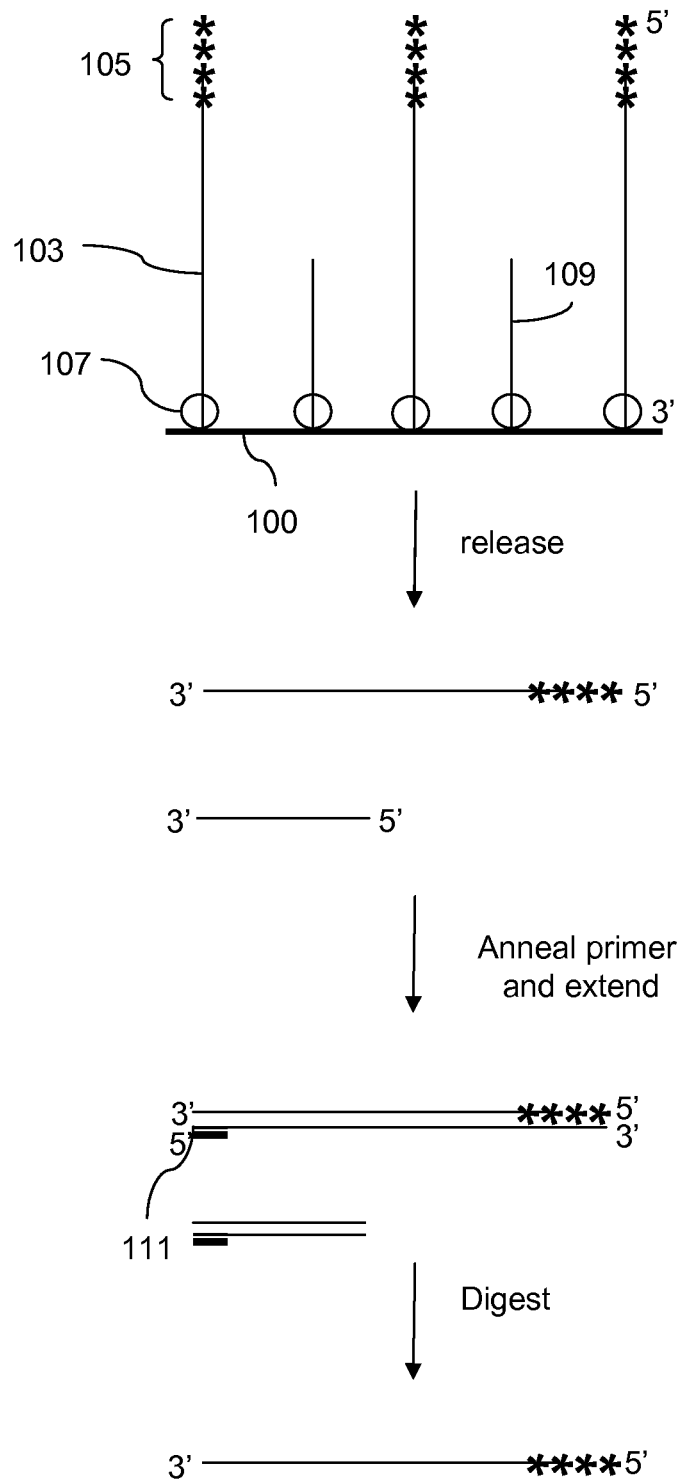
FIG. 1 shows synthesis of a mixture of full length and truncated oligonucleotides on a solid support. Truncated species are digested leaving primarily full length oligonucleotides.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, IRL Press, London, Nelson and Cox (2000), Lehninger, *Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses thereof are shown in U.S. Ser. Nos. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. No. 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. No. 10/063,559 (United States Publication No. US20020183936), 60/349,546, 60/376,003, 60/394,574 and 60/403,381.

B) Definitions

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

"Biopolymer" or "biological polymer" is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above. "Biopolymer synthesis" is intended to encompass the synthetic production, both organic and inorganic, of a biopolymer.

"Complementary" or "substantially complementary" refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementary exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa *Nucleic Acids Res.* 12:203 (1984), incorporated herein by reference.

A "combinatorial synthesis strategy" is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

"Effective amount" refers to an amount sufficient to induce a desired result.

"Genome" is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

Hybridization conditions will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization."

"Hybridization probes" are oligonucleotides capable of binding in a base-specific manner to a complementary strand of nucleic acid. Such probes include peptide nucleic acids, as described in Nielsen et al., *Science* 254, 1497-1500 (1991), and other nucleic acid analogs and nucleic acid mimetics. See U.S. Pat. No. 6,156,501.

"Hybridizing specifically to" refers to the binding, duplexing, or hybridizing of a molecule substantially to, or only to, a particular nucleotide sequence or sequences under stringent conditions when that sequence is present in a complex mixture (e.g., total cellular DNA or RNA).

"Isolated nucleic acid" is an object species that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

"Mixed population" or "complex population" refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

"Monomer" refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

Nucleic acids according to the present invention may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

Oligonucleotides may include modifications. Amino modifier reagents may be used to introduce a primary amino group into the oligo. A primary amino group is useful for a variety of coupling reactions that can be used to attach various labels to the oligo. The most frequently used labels are in the form of NHS-esters, which can couple with primary amino groups. A variety of derivatives of biotin are available in which the biotin moiety is connected (through the 4-carboxybutyl group) to a linker molecule that can be attached directly to an oligonucleotide. Fluorescent dies such as 6-FAM, HEX, TET, TAMRA, and ROX may be coupled to an oligo. Phosphate groups may be attached to the 5' and/or 3' end of an oligo. Oligos may also be phosphorothioated. A phosphorothioate group is a modified phosphate group with one of the oxygen atoms replaced by a sulfur atom. In a phosphorothioated oligo (often called an "S-Oligo"), some or all of the internucleotide phosphate groups are replaced by phosphorothioate groups. The modified "backbone" of an S-Oligo is resistant to the action of most exonucleases and endonucleases. In some embodiments the oligo is sulfurized only at the last few residues at each end of the oligo. This results in an oligo that is resistant to exonucleases, but has a natural DNA center. Degenerate bases may also be incorporated into an oligo. may also be incorporated into an oligo Additional modifications that are available include, for example, 2'O-Methyl RNA, 3'-Glyceryl, 3'-Terminators, Acrydite, Cholesterol labeling, Dabcyl, Digoxigenin labeling, Methylated nucleosides, Spacer Reagents, Thiol Modifications DeoxyInosine, DeoxyUridine and halogenated nucleosides.

A "probe" is a surface-immobilized molecule that can be recognized by a particular target. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies. See U.S. Pat. No. 6,582,908 for an example of arrays having all possible combinations of probes with 10, 12, and more bases.

"Primer" is a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

A "tag" or "tag sequence" is a selected nucleic acid with a specified nucleic acid sequence. A tag probe has a region that is complementary to a selected tag. A set of tags or a collection of tags is a collection of specified nucleic acids that may be of similar length and similar hybridization properties, for example similar $T_m$. The tags in a collection of tags bind to tag probes with minimal cross hybridization so that a single species of tag in the tag set accounts for the majority of tags which bind to a given tag probe species under hybridization conditions. For additional description of tags and tag probes and methods of selecting tags and tag probes see U.S. Ser. No. 08/626,285 and EP/0799897, each of which is incorporated herein by reference in their entirety.

"Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

A "target" is a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

"Restriction enzyme or endonuclease" A number of methods disclosed herein require the use of restriction enzymes to fragment the nucleic acid sample. In general, a restriction enzyme recognizes a specific nucleotide sequence of four to eight nucleotides and cuts the DNA at a site within or a specific distance from the recognition sequence. For example, the restriction enzyme EcoRI recognizes the sequence GAATTC and will cut a DNA molecule between the G and the first A. The length of the recognition sequence is roughly proportional to the frequency of occurrence of the site in the genome. A simplistic theoretical estimate is that a six base pair recognition sequence will occur once in every 4096 ($4^6$) base pairs while a four base pair recognition sequence will occur once every 256 ($4^4$) base pairs. In silico digestions of sequences from the Human Genome Project show that the actual occurrences may be more or less frequent, depending on the sequence of the restriction site. Because the restriction sites are rare, the appearance of shorter restriction fragments, for example those less than 1000 base pairs, is much less frequent than the appearance of longer fragments. Many different restriction enzymes are known and appropriate restriction enzymes can be selected for a desired result. (For a description of many restriction enzymes see, New England BioLabs Catalog which is herein incorporated by reference in its entirety for all purposes).

"Nicking endonucleases" are restriction enzymes that hydrolyze only one strand of the DNA duplex, to produce DNA molecules that are "nicked", rather than cleaved. The resulting nicks (3'-hydroxyl, 5'-phosphate) can serve as initiation points for further enzymatic reactions such as replacement DNA synthesis, strand-displacement amplification (Walker, G. T. et al. (1992) *Proc. Natl. Acad. Sci. USA* 89, 392-396.), exonucleolytic degradation or the creation of small gaps (Wang, H. and Hays, J. B. (2000) *Mol. Biotechnol.* 15, 97-104). These enzymes may occur naturally or they may be engineered or altered to nick. N.BstNB I occurs naturally and nicks because it is unable to form dimers. N.Alw I is a derivative of the restriction enzyme Alw I, that has been engineered to behave in the same way. These enzymes nick adjacent to their recognition sequences. N.BbvC IA and N.BbvC IB are derived from the heterodimeric restriction enzyme BbvC I, each has only one catalytic site so they nick within the recognition sequence but on opposite strands. In some embodiments newly engineered or discovered nicking enzymes are used. It is likely that the methods used to engineer existing nicking enzymes will be broadly applicable and many existing restriction enzymes may be engineered to produce corresponding nicking enzymes.

DNA Polymerase I Large (Klenow) Fragment consists of a single polypeptide chain (68 kDa) that lacks the 5'→3' exonuclease activity of intact *E. coli* DNA polymerase I, but retains its 5'→3' polymerase, 3'→5' exonuclease and strand displacement activities. The Klenow fragment has been used for strand displacement amplification (SDA). See, e.g., U.S. Pat. Nos. 6,379,888; 6,054,279; 5,919,630; 5,856,145; 5,846,726; 5,800,989; 5,766,852; 5,744,311; 5,736,365; 5,712,124; 5,702,926; 5,648,211; 5,641,633; 5,624,825; 5,593,867; 5,561,044; 5,550,025; 5,547,861; 5,536,649; 5,470,723; 5,455,166; 5,422,252; 5,270,184, all incorporated herein by reference. Phi29 (φ29) polymerase may also be used for strand displacement amplification. See, for example, U.S. Pat. Nos. 5,576,204, 5,854,033, 5,198,543, 5,001,050, 6,280, 949 and 6,642,034.

"Adaptor sequences" or "adaptors" are generally oligonucleotides of at least 5, 10, or 15 bases and preferably no more than 50 or 60 bases in length; however, they may be even longer, up to 100 or 200 bases. Adaptor sequences may be synthesized using any methods known to those of skill in the art. For the purposes of this invention they may, as options, comprise primer binding sites, recognition sites for endonucleases, common sequences and promoters. The adaptor may be entirely or substantially double stranded. A double stranded adaptor may comprise two oligonucleotides that are at least partially complementary. The adaptor may be phosphorylated or unphosphorylated on one or both strands. Adaptors may be more efficiently ligated to fragments if they comprise a substantially double stranded region and a short single stranded region which is complementary to the single stranded region created by digestion with a restriction enzyme. For example, when DNA is digested with the restriction enzyme EcoRI the resulting double stranded fragments are flanked at either end by the single stranded overhang 5'-AATT-3', an adaptor that carries a single stranded overhang 5'-AATT-3' will hybridize to the fragment through complementarity between the overhanging regions. This "sticky end" hybridization of the adaptor to the fragment may facilitate ligation of the adaptor to the fragment but blunt ended ligation is also possible. Blunt ends can be converted to sticky ends using the exonuclease activity of the Klenow fragment. For example when DNA is digested with PvuII the blunt ends can be converted to a two base pair overhang by incubating the fragments with Klenow in the presence of dTTP and dCTP. Overhangs may also be converted to blunt ends by filling in an overhang or removing an overhang.

Oligonucleotides may be released from the array using a releasable group or a selectively cleavable portion or linker. The linker may be cleaved by, for example, enzymatic or chemical means. The oligonucleotide may be attached to the solid support via the releasable group so that activation or cleavage of the releasable group results in release of the oligonucleotide from the array. See, U.S. patent application Ser. Nos. 10/272,155 and 60/434,144. The releasable group may include a moiety or chemical group that is labile, i.e., may be activated or cleaved under a given set of conditions, but is stable under other sets of conditions. A reversible linker or an enzymatic release mechanism, such as an endonuclease may be used. Release may be mediated by any available mechanism. Enzymatic methods include, for example, use of an endonuclease or uracil DNA glycosylase (UDG) or (UNG). UNG catalyzes the hydrolysis of DNA that contains deoxyuridine at the site the uridine is incorporated. Incorporation of one or more uridines in the oligonucleotide followed by treatment with UNG will result in release of the oligonucleotide from the solid support. Linkers that may be cleaved by chemical means include, for example, disulfide linkers that may be reduced for release, 1,2-diol linkers which may be released by periodate treatment or a linker that is labile under acidic or basic conditions may be used. Releasable linkers may also be activatable by light of a certain wavelength or by exposure to high temperatures. The oligonucleotide may also have a restriction site incorporated in the 3' region so that the oligonucleotide may be made double stranded on the array and cleaved with a restriction endonuclease.

C) Methods for Synthesizing Oligonucleotides

Many molecular biology methods employ the use of oligonucleotides. They may be used, for example, as probes to detect the presence of a sequence, as primers that can be extended by one or more bases, as modifiable indicators of the presence of a specific ligand, to introduce changes into a sequence of interest, for example, point mutation, insertion of a restriction site or insertion of a priming site, or as anchors that may be used to capture ligands. In many applications pools of many different oligonucleotides may be used.

When oligonucleotides are synthesized on a solid support a mixture of full-length species and shorter, truncated, capped species may be generated. For many applications it is desirable to enrich for full length species. Methods for enrichment of full length species and for synthesis of multiple copies of a complementary strand are disclosed.

The synthesized oligonucleotide may contain in the 3' to 5' direction a cleavable linker, a recognition sequence for a nicking endonuclease, a common adapter sequence and a specific sequence, for example, a locus specific sequence. In a preferred embodiment the 5' end of the synthesized oligonucleotide is resistant to digestion by a nuclease. In a particularly preferred embodiment the last 4 bases of the synthesized oligonucleotide contain a phosphorothioate linkage rather than a phosphodiester linkage. The presence of multiple phosphorothioate linkages at or near the 5' end of the synthesized oligonucleotide renders the oligonucleotide resistant to cleavage by nucleases that digest in a 5' to 3' direction.

Following synthesis, the synthesized oligonucleotides may be released from the array into solution using, for example, the cleavable linker. A first primer complementary to the 3' end of the synthesized oligonucleotides may then be annealed to the released oligonucleotides and extended. This converts the synthesized oligonucleotides to a double stranded form. The population may then be treated with an exonuclease. In a preferred embodiment the T7 gene 6 exonuclease is used, this is a 5' to 3' double strand specific exonuclease. The enzyme is completely inhibited by four phosphorothioates, Nikiforov et al. (1994) *PCR Methods and Applications* 3(5):285-291. This treatment results in digestion of shorter species which lack the four phosphorothioate bases, leaving primarily the full length species of synthesized oligonucleotides. Other exonucleases may also be used, for example, Lambda exonuclease and RecJ$_f$.

In a preferred embodiment the remaining oligonucleotides are then amplified. A primer, which may be the same as the first primer, is annealed to the remaining oligonucleotides and extended. The newly synthesized strand is nicked by, for example, a nicking enzyme that recognized a site in the sequence. Nicking generates a 5' portion with a free 3' hydroxyl and a polymerase with strand displacement activity, such as phi29, is used to extend the 5' portion. The 3' portion is displaced and a new 3' portion is synthesized in its place. The process of nicking, extension and displacement can be repeated multiple times. Nicking and extension may take place in the same reaction so that when the nicking site is regenerated by extension of the 5' portion it may be cleaved and extension may begin again. This allows a linear amplification of the 3' portion. This portion may contain, for example, a common sequence that may be used as for priming amplification, a locus specific sequence, and a restriction site. The amplified oligonucleotides may be used, for example, in solution based genotyping or for multiplex amplification. For a discussion of genotyping methods that use oligonucleotides, see Syvanen, *Nature Rev. Gen.* 2:930-942 (2001).

Cleavage at the nicking site generates a free 3' hydroxyl in the copy strand which can act as a primer. The primer may then be extended using a strand displacing polymerase. As the primer is extended it displaces the remaining copy strand bound to the oligonucleotide. The cleavage and extension reactions are repeated for a plurality of cycles in a preferred embodiment. At each cycle a copy of the 3' portion of the copy strand (lacking the region that is 5' of the nicking site) is released. This is complementary to the 3' portion of the full length oligonucleotide.

FIG. 1 illustrates a method to enrich for full length oligonucleotides (103). The oligonucleotides are synthesized, for example, on a solid support (100). The oligonucleotides are synthesized so full length probes (103) have a nuclease resistant portion (105) that is not present in truncated probes (109). After synthesis the oligonucleotides are released from the solid support by cleaving a releasable portion (107). After release the oligonucleotides are mixed with a primer (111) that is complementary to the 3' end of the oligonucleotides. The primer is extended, resulting in double stranded oligonucleotides. The double stranded oligonucleotides are then mixed with a nuclease, for example, T7 gene 6 nuclease which is a 5' to 3' exonuclease specific for double stranded DNA. See, Engler, M. J., and Richardson, C. C, *J. Biol. Chem.* 258, 11197-11205 (1983). Oligonucleotides that lack the nuclease resistant feature, four phosphorothioate linkages in a preferred embodiment, are digested by the nuclease, while full length oligonucleotides are resistant to cleavage and are not digested. Both strands of double stranded oligonucleotides that are not full length are digested and the newly synthesized strand of the double stranded full length oligonucleotides is digested. The resulting mixture is enriched for single stranded full length oligonucleotides.

Figure 2:
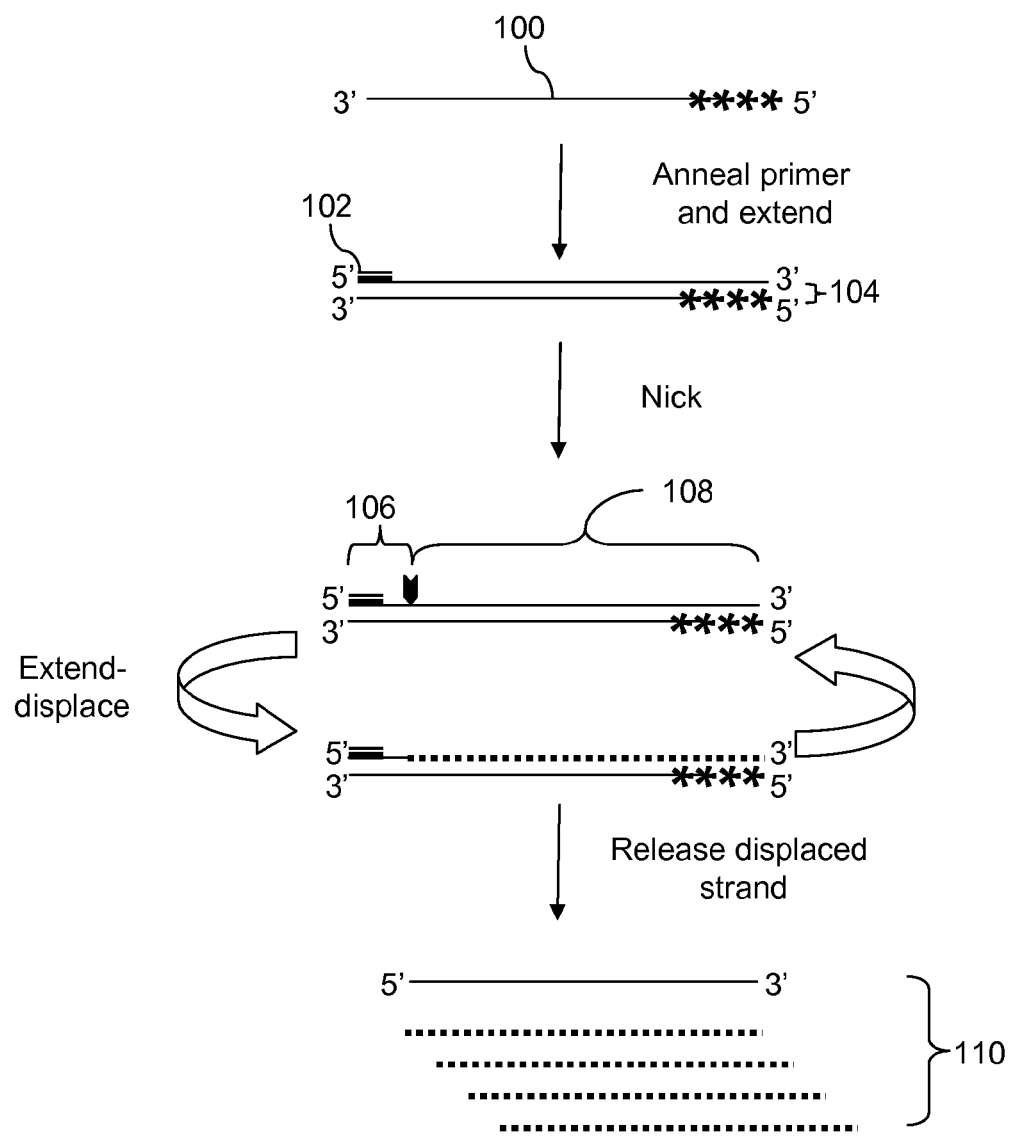
FIG. 2 shows amplification of full length oligonucleotides using a nicking enzyme and strand displacement.

In FIG. 2 a method for amplifying the full length oligonucleotides is shown. In this embodiment a template oligonucleotide is synthesized on the array and the sequence of interest to be produced in large amounts is the complement of the portion of the template oligonucleotide that is 5' of the nicking site. The sample enriched for full length oligonucleotides (100) is mixed with at least one primer (102) that is complementary to the 3' end of at least some of the oligonucleotides. The primer is extended generating double stranded oligonucleotides (104). The double stranded oligonucleotides are nicked in the newly synthesized strand generating a 5' portion with a free 3' hydroxyl (106) and a 3' portion (108). In a preferred embodiment the 3' portion contains the sequence or sequences to be amplified. The 5' portion may then be extended using, for example, a strand displacing polymerase so that the 3' portion is displaced and released. Multiple rounds of nicking and extension result in release of multiple copies of the 3' portion (110). For example, if the template oligonucleotide synthesized on the array is 5' cttgtctggt cccacagttc tccctttagt gagggttaat t*nnnngatcc 3' (SEQ ID NO: 1) where the site of cleavage at the nicking site is indicated by * the sequence of interest to be amplified is 5' aattaaccct cactaaaggg agaactgtgg gaccagacaa g 3' (SEQ ID NO: 2). In a preferred embodiment there are a plurality of different template oligonucleotides and amplification results in a plurality of different amplified sequences of interest.

Figure 3:
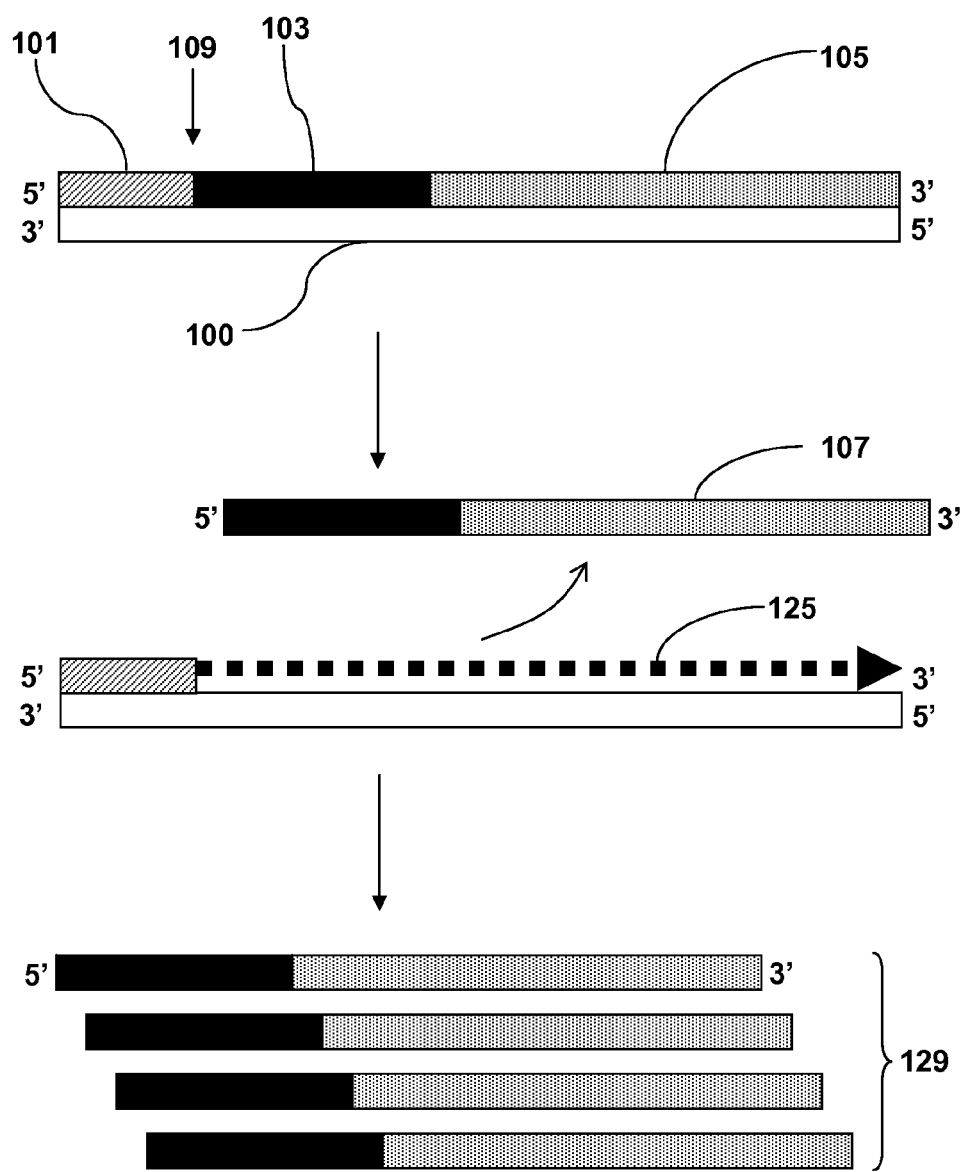
FIG. 3 shows a template oligonucleotide (100) and the amplification product (107) resulting from amplification using the method shown in FIG. 2.

FIG. 3 shows amplification using template oligonucleotide (100). Template oligonucleotides may be synthesized and enriched for full length oligonucleotides. A primer that is complementary to the 3' end of the full length oligonucleotides may be hybridized to the oligonucleotide and extended to generate complements of the full length oligonucleotides. The complements may then be cleaved at nicking position (109) thus generating a 5' portion (101) that can be extended, forming newly synthesized strand (125) and a 3' portion, the amplified sequence (107), that will be displaced when the 5' portion (101) is extended. In a preferred embodiment the amplified sequence comprises a portion that is common to a plurality of amplified sequences (103) and a portion that is unique to each amplified sequence (105). Multiple rounds of nicking, extension of 101 and displacement of 107 result in amplification, resulting in many copies of the displaced segment (129).

In a preferred embodiment a plurality of different template oligonucleotides (100) are synthesized and amplification results in amplification of a plurality of different amplified sequences (107). There may be, for example, more than 1,000, 5,000, 10,000, 100,000 or 1,000,000 different amplified sequences. In a preferred embodiment a plurality of different amplified sequences each sharing a common priming site in 103 are synthesized. The sequence 103 may also comprise a tag sequence, a promoter sequence, or a recognition site for a restriction enzyme. Tag sequences are described in U.S. Pat. No. 6,458,530 and U.S. patent application Ser. No. 09/827,383.

The amplified sequences may be used, for example, for multiplex amplification, for SBE genotype analysis, for OLA genotype analysis, or for multiplexed anchored runoff amplification (MARA) as described in U.S. patent application Ser. No. 10/272,155. For methods of using oligonucleotides see, for example, U.S. Pat. Nos. 5,856,092, 6,638,719, 5,935,793 and 5,242,794 and U.S. patent application Ser. No. 09/419,817. The amplified sequences may be used, for example, for primer extension, PCR, locus specific amplification, genotyping, isothermal amplification, for reverse transcription of RNA or for RT-PCR. The method may be used to amplify one sequence or more than one sequence. In preferred embodiments more than 1000, 10,000, 100,000, 1,000,000 or 2,000,000 different sequences are amplified.

In one embodiment the oligonucleotides and amplified sequences may be used to amplify genomic fragments. The amplified fragments may then be used, for example, for genotyping by, for example, allele specific hybridization to an array of probes that interrogates genotype. The methods may be used to synthesize a plurality of oligonucleotides that have a 3' locus specific portion and a 5' portion that comprises a nicking site, for example a recognition site for a nicking restriction enzyme. The locus specific portions may hybridize to a plurality of preselected regions in the genome so that amplification with these locus specific primers results in amplification of fragments of the genome that contain known polymorphisms. The plurality of oligonucleotides may be used to amplify genomic fragments in a first round of amplification and then the fragments may be nicked and amplified using a strand displacing DNA polymerase. The amplification may comprise one or more isothermal steps. See also, U.S. patent application Ser. Nos. 60/508,418, 10/318,692, 10/442,021, and 10/681,773.

In a preferred embodiment the amplification is isothermal amplification. The methods employ a nicking step, in which one strand of a double stranded nucleic acid is cleaved while the other strand is left in tact, and an extension step. The methods preferably employ multiple rounds of nicking followed by extension of the 3' hydroxyl generated by the nicking. Nicking may be accomplished by, for example, use of a nicking endonuclease or by use of a restriction enzyme that cleaves both strands, but cleavage of one strand is blocked by use of a modified base. In many embodiments a DNA polymerase having strand displacing activity and lacking 5'-3' exonuclease activity (such as the DNA Polymerase I Large (Klenow) Fragment or similar enzymes) is used. See also U.S. patent application Ser. Nos. 10/318,692 and 60/508,418.

In one embodiment a method to synthesize full length oligonucleotides is disclosed. Template oligonucleotides are synthesized on a solid support in a 3' to 5' direction. The template oligonucleotides have in the 3' to 5' direction, a linker region that attaches the oligonucleotide to the solid support, a primer binding site, a nicking restriction enzyme recognition site and a sequence of interest. The sequence that is amplified is the complement of the 5' portion of the full length template oligonucleotide.

In one embodiment a plurality of oligonucleotides is synthesized on a solid support so that many different oligonucleotide sequences are synthesized simultaneously. Many copies of ach sequence may be synthesized on the array. There may be, for example, more than 5,000, 10,000, 100,000, 500,000, 1 million, or 2.5 million different oligonucleotide sequences synthesized on a single array, with multiple copies of each sequence being synthesized. The oligonucleotides synthesized on the array and enriched for full length sequences may be used, for example, as locus specific primers in a genotyping assay. In another embodiment the oligonucleotides synthesized on the array and enriched for full length sequences are subjected to an amplification step as described above, so that copies of the complement of the 5' portion of the oligonucleotides may be generated.

Although many of the embodiments described depict release of the oligonucleotides from the array prior to subsequent enrichment and amplification steps, these steps may also be performed while the oligonucleotides are attached to the array. In one embodiment, oligonucleotides are synthesized on a solid support so that full length oligonucleotides are resistant to nuclease digestion. Oligonucleotides that are not resistant to nuclease digestion are digested with a nuclease. In a preferred embodiment the oligonucleotides on the array are made double stranded by, for example, hybridization of a primer to the 3' portion and extension of the primer. A nuclease that digests double stranded DNA 5' to 3', such as T7 gene 6 exonuclease, may be used. After digestion the remaining oligonucleotides may be released from the array.

In another embodiment oligonucleotides are amplified on an array. Template oligonucleotides are synthesized on an array and made double stranded. The double stranded oligonucleotide is nicked and the 5' portion of the nicked strand is extended, displacing the 3' portion of the nicked strand. The nicking site is regenerated and can be nicked again and extended again releasing the 3' portion again. This cycle of nicking-extension and release may be repeated for multiple cycles, resulting in amplification of the portion that is 3' of the nicking site. This may be done while the template oligonucleotide is attached to a solid support or the template oligonucleotides may be released from the solid support prior to amplification. A step for removal of truncated oligonucleotide species may also be included.

In one embodiment a kit is disclosed. The kit may comprise a plurality of oligonucleotides comprising in the 5' to 3' direction, a locus specific region that is variable between different oligonucleotides in the plurality, a first common priming site, a nicking site, and a second common priming site. The oligonucleotides of the kit may be amplified according to the methods disclosed above to generate amplified nucleic acids complementary the region of the oligonucleotides that is 5' of the recognition site for the nicking enzyme. The oligonucleotides may be free in solution or attached to a solid support.

EXAMPLE

Cleavage of Oligonucleotides from Array Using 1,2-Diol Cleavable Linker

Synthesize oligonucleotides on an array including a 1,2-diol linker. Prepare a fresh solution of 10 mM Na Periodate in 100 mM NaOAc pH 6.0 by first preparing 50 mM Na Periodate stock solution, 50 mM Na Periodate stock solution is 0.125 g Na Periodate (MW=213.9) in 11.7 ml of 100 mM NaOAc pH 6.0. Dilute this stock solution 1:5 (1 ml 50 mM Na Periodate+4 ml 100 mM NaOAc pH 6.0) Inject enough volume to cover array surface (~200 μl) and incubate at room temperature (25° C.) for 30 minutes. Withdraw solution from array surface and pass over G-25 Sephadex column to purify nucleic acid sequence.

Enrichment of full-length sequences. Convert single strand oligonucleotides to double-stranded form by mixing 10 μl Water, 2.5 μl 10× Taq Gold Buffer, 2 μl 25 mM $MgCl_2$, 2.5 μl 10× dNTPs, 5 μl 100 μM primer, 0.25 μl Amplitaq Gold and 2.5 μl cleavage product and incubate at 95° C. for 2 min, 55° C. for 2 min and 72° C. for 6 min, then hold at 4° C. Pass the reaction over a G-25 Sephadex column to exchange the buffer. Add 5 μl of 10× T7 Gene 6 Exonuclease Buffer (USB) (5× buffer contains 200 mM Tris-HCl pH 7.5, 100 mM $MgCl_2$, 250 mM NaCl). Add 2 μL of T7 Gene 6 Exonuclease (USB) and incubate at 37° C. for 60 min then hold at 4° C. Pass the reaction over a G-25 Sephadex column to exchange the buffer.

Amplification of Full-Length Enriched Oligonucleotides

Convert enriched single strand oligonucleotides to double-stranded form as described above. Mix 21.2 μL Water, 3 μL 10×DNA pol I Large Fragment (Klenow) Buffer, 0.35 μM NaCl, 3 μL 10× dNTPs, 0.5 μL double stranded enriched oligo, 1 μL N. Alw I (NEB), and 1 μL Klenow (NEB). Incubate at 37° C. for 6 hours to overnight. Check aliquot of reaction on 10%, 15%, or 20% Denaturing (8 M urea) acrylamide Gel. Pass the reaction over a G-25 Sephadex column to exchange the buffer.

CONCLUSION

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

I claim:

1. A method of making a plurality of single stranded oligonucleotides, which comprises:
    synthesizing a plurality of single stranded oligonucleotides on a solid support, wherein the plurality of single stranded oligonucleotides comprises a plurality of full length oligonucleotides and at least one truncated oligonucleotide, wherein the full length oligonucleotides comprise at least one terminal phosphorothioate linkage, and wherein the at least one terminal phosphorothioate linkage confers exonuclease resistance to the full length oligonucleotides; and
    digesting the at least one truncated oligonucleotide with an exonuclease, wherein the exonuclease is capable of digesting single stranded oligonucleotides.

2. The method of claim 1, additionally comprising:
    releasing the full length oligonucleotides from the solid support by cleaving a cleavable portion of the oligonucleotides.

3. The method of claim 2, wherein the cleavable portion comprises uracil.

4. The method of claim 3, wherein uracil DNA glycosylase is used to generate an abasic site and the full length oligonucleotides are released by cleavage at the abasic site.

5. The method of claim 1, wherein the full length oligonucleotides comprise at least four terminal phosphorothioate linkages.

6. The method of claim 1, wherein the exonuclease cleaves 5' to 3'.

7. The method of claim 6, wherein the exonuclease is a RecJ$_f$ exonuclease.

8. The method of claim 1, wherein the full length oligonucleotides comprise an adaptor sequence.

9. The method of claim 8, wherein the adaptor sequence comprises a primer binding site.

10. The method of claim 8, wherein the adaptor sequence comprises a recognition site for an endonuclease.

11. The method of claim 1, wherein the plurality of full length oligonucleotides comprises at least 1000 different sequences.

12. The method of claim 1, wherein the synthesis strategy for the oligonucleotides is combinatorial masking.

13. A method of making a plurality of single stranded oligonucleotides, comprising:
    synthesizing a plurality of single stranded oligonucleotides on a solid support, wherein the single stranded oligonucleotides are synthesized on the solid support in a 3' to 5' direction, wherein each single stranded oligonucleotide comprises, in the 3' to 5' direction, a cleavable portion, an adaptor sequence, a sequence of interest, and a 5' end that comprises at least one terminal phosphorothioate linkage, and wherein the at least one terminal phosphorothioate linkage confers exonuclease resistance to the 5' end.

14. The method of claim 13, wherein the 5' end of the single stranded oligonucleotides comprises at least four terminal phosphorothioate linkages.

15. The method of claim 13, wherein the cleavable portion comprises uracil.

16. The method of claim 13, wherein the adaptor sequence comprises a primer binding site.

17. The method of claim 13, wherein the adaptor sequence comprises a recognition site for an endonuclease.

18. The method of claim 13, wherein the plurality of single stranded oligonucleotides on the solid support comprises at least 1000 different sequences.

19. The method of claim 13, wherein the synthesis strategy for the single stranded oligonucleotides is combinatorial masking.

20. A synthesized single stranded oligonucleotide, comprising in the 3' to 5' direction: a cleavable portion comprising uracil, an adaptor sequence, a sequence of interest, and a 5' end that comprises at least one terminal phosphorothioate linkage, wherein the at least one terminal phosphorothioate linkage is designed to confer exonuclease resistance to the 5' end, wherein the adaptor sequence comprises a recognition site for an endonuclease.

21. The single stranded oligonucleotide of claim 20, wherein the 5' end comprises at least four terminal phosphorothioate linkages.

22. The single stranded oligonucleotide of claim 20, wherein the adaptor sequence comprises a primer binding site.

23. The single stranded oligonucleotide of claim 20, wherein the oligonucleotide is synthesized by combinatorial masking.

* * * * *